United States Patent

Wang et al.

[11] Patent Number: 5,844,669
[45] Date of Patent: Dec. 1, 1998

[54] DETECTING AND MINIMIZING FIBER MISALIGNMENT IN A COMPOSITE DURING MANUFACTURING

[75] Inventors: Weiping Wang; Thomas Huei Hwang, both of Schenectady; Emily Yxie Shu, Niskayuna, all of N.Y.; Richard Alan Ridilla, Hudson, N.H.; Michael Evans Graham, Slingerlands, N.Y.; Michael Kent Cueman, Niskayuna, N.Y.; Meng-Ling Hsiao, Schenectady, N.Y.; Charles Richard Evans, Cincinnati, Ohio

[73] Assignee: General Electric Company, Schenectady, N.Y.

[21] Appl. No.: 763,773

[22] Filed: Dec. 11, 1996

Related U.S. Application Data

[60] Provisional application No. 60/022,243 Jul. 22, 1996.
[51] Int. Cl.⁶ .................................................. G01N 21/88
[52] U.S. Cl. ........................................ 356/72; 250/227.16
[58] Field of Search ......................... 356/72; 250/227.16

[56] References Cited

U.S. PATENT DOCUMENTS

| | | | |
|---|---|---|---|
| 5,118,931 | 6/1992 | Udd et al. | 250/227.16 |
| 5,279,892 | 1/1994 | Baldwin et al. | 428/257 |
| 5,604,836 | 2/1997 | Dunphy et al. | 385/92 |

*Primary Examiner*—Vincent P. McGraw
*Attorney, Agent, or Firm*—Douglas E. Erickson; Marvin Snyder

[57] ABSTRACT

A method for detecting misalignment of initially-aligned fiber filaments in a composite. An optical fiber is placed among the fiber filaments in the composite, light is directed into the optical fiber, the intensity of the light in the optical fiber is measured during subsequent composite processing, and attenuation in such light intensity is ascertained which indicates such misalignment (e.g., wrinkling, bending, buckling, porosity, delamination and the like) is being detected during such processing. In another preferred method, before-processing and after-processing x-ray images are taken of an x-ray-attenuating fiber which has been placed among x-ray-transparent fiber filaments in a composite.

18 Claims, 4 Drawing Sheets

DETECTING AND MINIMIZING FIBER MISALIGNMENT IN A COMPOSITE DURING MANUFACTURING

This application claims priority of a Provisional application entitled "Fiber Optic Bend Sensor For In-Process Monitoring Of Polymeric Composites" by Weiping Wang et al., Ser. No. 60/022,243 filed Jul. 22, 1996.

BACKGROUND OF THE INVENTION

The present invention relates generally to manufacturing composites, and more particularly to a method for detecting misalignment of composite fiber filaments during, and due to, processing (i.e., manufacturing) of the composite.

A "composite" is defined to be a material having any (metal or non-metal) fiber filament embedded in any (metal or non-metal) matrix binder. The term "metal" includes an alloy. An example of a composite is a material having graphite filaments embedded in an epoxy matrix binder. Because of their light weight and great strength, composites are being considered for use in diverse applications, such as in aircraft engine fan blades.

For critical structural applications of composites, the presence of defects, even in small amounts, is detrimental to the mechanical performance of the composites. Misalignment of initially-precisely-aligned fibers within the matrix binder during subsequent processing of a composite (such as, for example, during a subsequent compression molding process) leads to a manufactured composite which can suffer from wrinkling, bending, buckling, porosity, delamination and the like. Conventional ultrasonic scanning or x-ray CT is effective at analyzing composites in the cured state but is not effective at analyzing composites during processing due to the presence of the forming apparatus (e.g., mold or autoclave) surrounding the composites during manufacture.

What is needed is a method for detecting fiber misalignment in a composite during, and due to, the composite manufacturing process which can be used to evaluate changes in manufacturing parameters (e.g., changes in compression-mold closing speed) which can lead to defect-free manufactured composites.

SUMMARY OF THE INVENTION

It is an object of the invention to provide a method for detecting fiber misalignment during, and due to, composite manufacturing.

A first preferred method of the invention is for detecting misalignment of initially-generally-aligned fiber filaments in a composite during subsequent processing of the composite. The first preferred method includes sequential steps a) through d). Step a) includes placing at least a portion of an optical fiber among the fiber filaments in the composite before the subsequent processing of the composite. Step b) includes directing light from a first location in the optical fiber towards a second location in the optical fiber during the subsequent processing of the composite. Step c) includes measuring the intensity of the light from the second location during the subsequent processing of the composite. Step d) includes ascertaining if the measured light intensity is attenuated at any time during the subsequent processing of the composite, such attenuation indicating misalignment at such time of the fiber filaments during the subsequent processing of the composite.

A second preferred method of the invention is for detecting misalignment of initially-generally-aligned fiber filaments in a composite during subsequent processing of the composite. The second preferred method includes sequential steps a) through e). Step a) includes placing at least a portion of an optical fiber among the fiber filaments in the composite before the subsequent processing of the composite. Step b) includes directing light from a first location in the optical fiber towards a second location in the optical fiber during the subsequent processing of the composite. Step c) includes reflecting the light from the second location towards the first location in the optical fiber. Step d) includes measuring the intensity of the light reflected from the second location during the subsequent processing of the composite. Step e) includes ascertaining if the measured light intensity is attenuated at any time during the subsequent processing of the composite, such attenuation indicating misalignment at such time of the fiber filaments during the subsequent processing of the composite.

A third preferred method of the invention is for detecting misalignment of initially-generally-aligned, x-ray-transparent fiber filaments in a composite due to subsequent processing of the composite. The third preferred method includes sequential steps a) through d). Step a) includes placing at least a portion of an x-ray-attenuating fiber among the x-ray-transparent fiber filaments in the composite before the subsequent processing of the composite. Step b) includes taking a first x-ray image of the composite showing the shape of the x-ray-attenuating fiber before the start of the subsequent processing of the composite. Step c) includes taking a second x-ray image of the composite showing the shape of the x-ray-attenuating fiber after the start of the subsequent processing of the composite. Step d) includes ascertaining from the first and second x-ray images if any change in shape of the x-ray-attenuating fiber exists, such change in shape indicating misalignment of the x-ray-transparent fiber filaments in the composite due to the subsequent processing of the composite.

Several benefits and advantages are derived from the method of the invention. The first and second preferred methods of the invention determine misalignment of the fiber filaments of a composite while the composite is being manufactured. This can lead to controlling the manufacturing parameters during the manufacturing process to minimize fiber filament misalignment and hence to minimize composite defects such as, but not limited to, wrinkling and delamination. The third preferred method of the invention determines fiber filament misalignment after a composite processing step has been completed and can be used as a final quality check on the manufactured composite.

BRIEF DESCRIPTION OF THE DRAWINGS

The accompanying drawings illustrate the present invention wherein.

DETAILED DESCRIPTION OF THE INVENTION

Figure 1:
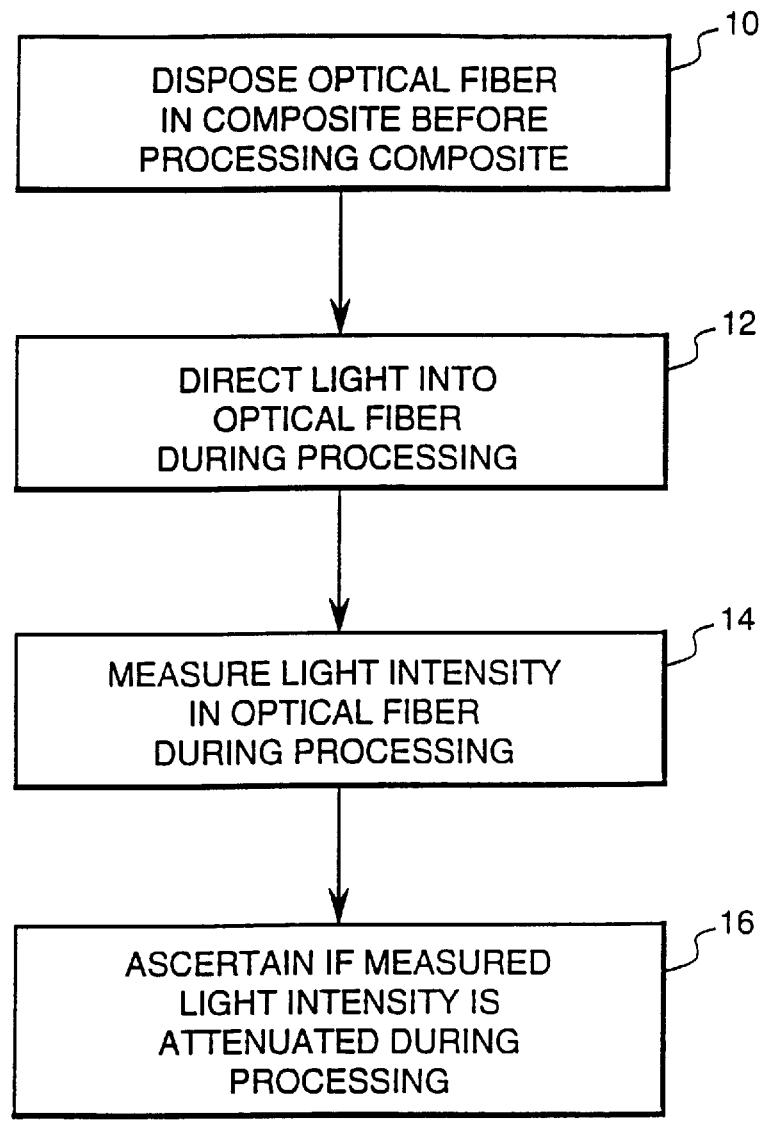
FIG. 1 is a flow chart of a first preferred method of the present invention for detecting fiber misalignment during composite manufacturing.

Referring now to the drawings, FIG. 1 shows a flow chart of a first preferred method of the invention for detecting misalignment of initially-generally-aligned fiber filaments in a composite during subsequent processing of the composite. By "generally aligned" is meant generally straight and generally parallel. As previously stated, a "composite" is defined to be a material having any (metal or non-metal) fiber filament embedded in any (metal or non-metal) matrix binder. The term "metal" includes an alloy. A preferred composite includes multiple laminations each consisting essentially of (and preferably consisting of) graphite fiber filaments embedded in an epoxy matrix binder. Composite processing is defined to be one or more of the steps required to manufacture a composite. A preferred composite processing consists essentially of compression molding the previously-described multiple laminations into an aircraft engine fan blade.

The first preferred method of the invention includes sequential steps a) through d).

Step a) is portrayed in block 10 of FIG. 1 as "Dispose Optical Fiber In Composite Before Processing Composite". Step a) includes disposing at least a portion of an optical fiber among the fiber filaments in the composite before the subsequent processing of the composite. As is known to those skilled in the art, an optical fiber includes a core surrounded by a cladding wherein light travels in the core along the core's longitudinal axis and wherein off-axis light strikes the cladding essentially at angles (measured from a normal to the cladding) greater than the angle of reflection (measured from a normal to the cladding) between the typically-higher-index-of-refraction core and the typically-lower-index-of-refraction cladding so that such off-axis light essentially is reflected back into the core. Such reflection occurs when the flexible optical fiber is essentially straight. When the optical fiber is bent, its longitudinal axis is no longer straight, and significant amounts of off-axis light in the core will strike the surrounding cladding at angles (measured from a normal to the cladding) less than such angle of reflection and be refracted into the cladding instead of being reflected back into the core. Thus, the intensity of light will decrease because of such bend in the optical fiber. Preferably, step a) also includes generally aligning at least a part of the portion of the optical fiber with the fiber filaments in the composite before the subsequent processing of the composite. This will allow any subsequent bending of the optical fiber to more closely match any subsequent misalignment of the fiber filaments.

Step b) is portrayed in block 12 of FIG. 1 as "Direct Light Into Optical Fiber During Processing". Step b) includes directing light from a first location in the optical fiber towards a second location in the optical fiber during the subsequent processing of the composite. Any light, including a laser light, may be used. However, for cost and other reasons, a preferred light is spectral light having a predetermined frequency bandwidth. Preferably, for ease of measurement, the first location is a first end of the optical fiber, the second location is a second end of the optical fiber, and the first end and second end are disposed outside and spaced apart from the composite. More precisely, it is preferred that the first and second locations also be centered on the longitudinal axis of the optical fiber.

Step c) is portrayed in block 14 of FIG. 1 as "Measure Light Intensity In Optical Fiber During Processing". Step c) includes measuring the intensity of the light from the second location during the subsequent processing of the composite. Any light-intensity sensor may be used such as, but not limited to, a photo-voltaic device which can give continuous analog or digital readings throughout the subsequent processing. Preferably, the light-intensity sensor is coaxially aligned with the longitudinal axis of the optical fiber, is disposed proximate the second location, and points towards the first location.

Step d) is portrayed in block 16 of FIG. 1 as "Ascertain If Measured Light Intensity Is Attenuated During Processing". Step d) includes ascertaining if the measured light intensity is attenuated at any time during the subsequent processing of the composite, such attenuation indicating misalignment at such time of the fiber filaments during such subsequent processing of the composite. Preferably, such ascertaining is performed automatically by a suitably-programmed computer whose input is a series of paired times and measured light intensities, as can be appreciated by those skilled in the art. Applicants have found that ascertained attenuation of at least forty percent in step d) indicates misalignment of the fiber filaments in the form of wrinkle formation during such subsequent processing of the composite.

In an exemplary method, which is also for minimizing such misalignment, the subsequent processing includes a process parameter which is controlled as a function of the attenuation ascertained in step d). Preferably, the subsequent processing includes compression molding, and the process parameter includes mold closure speed. Here, the mold closure speed is reduced at the beginning of misalignment detection, and the mold closure speed is increased (up to some predetermined limit) as long as the beginning of misalignment is not being detected.

Figure 2:
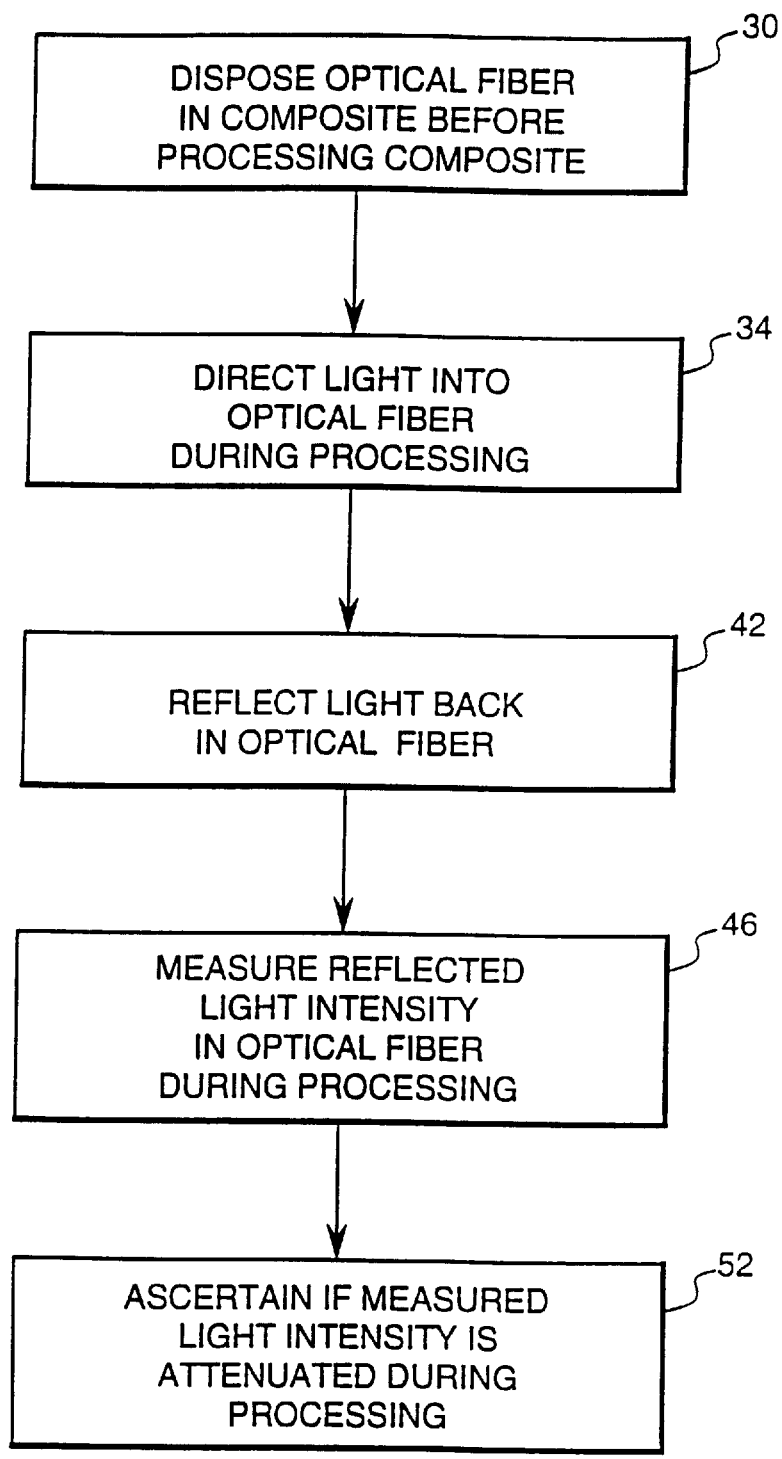
FIG. 2 is a flow chart of a second preferred method of the present invention for detecting fiber misalignment during composite manufacturing.
Figure 3:
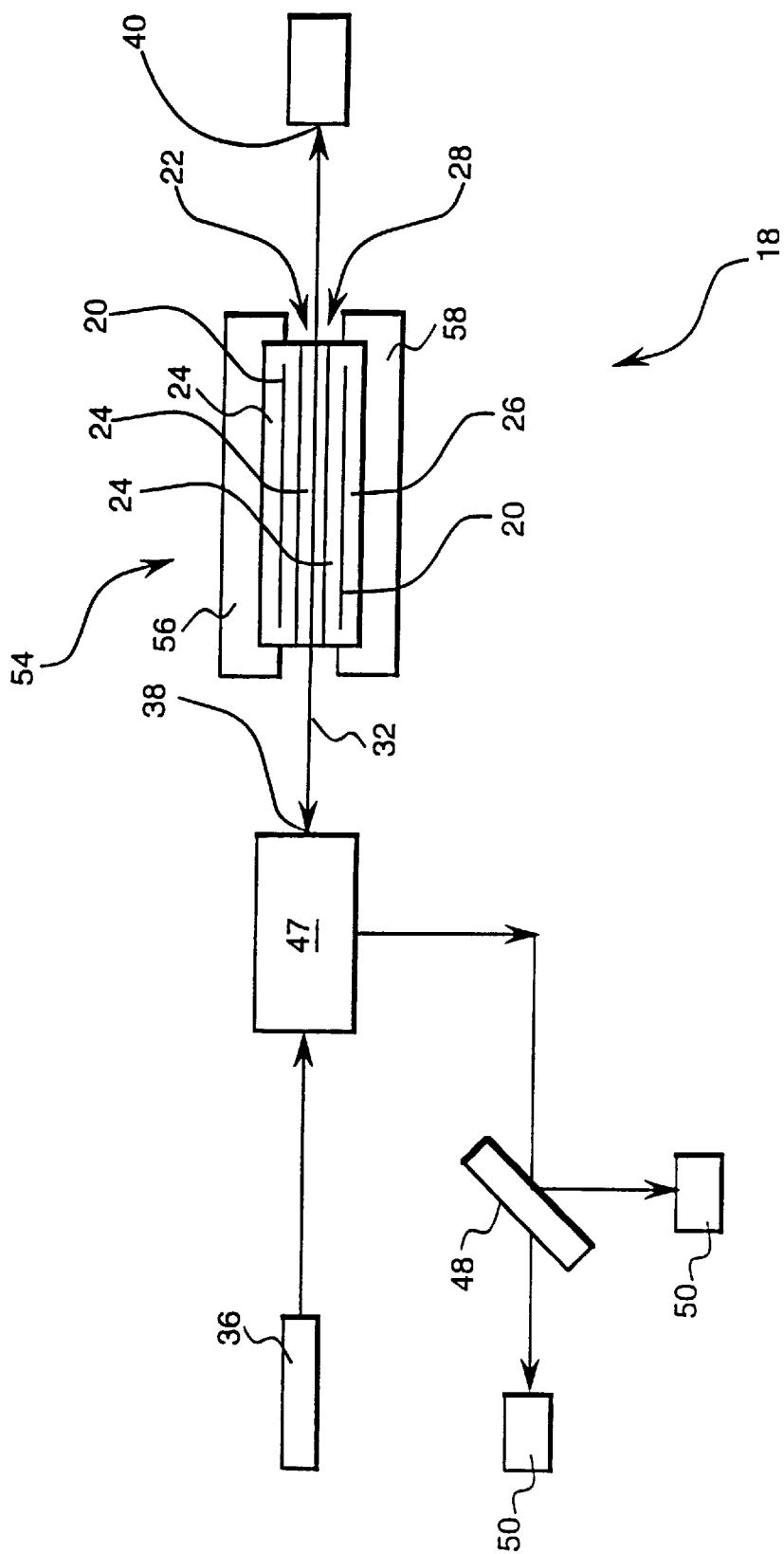
FIG. 3 is a schematic block diagram view of preferred apparatus for carrying out the second preferred method of FIG. 2.

Referring again to the drawings, FIG. 2 shows a flow chart of a second preferred method of the invention, and FIG. 3 shows preferred apparatus 18 for carrying out the second preferred method. The second preferred method is for detecting misalignment of initially-generally-aligned fiber filaments 20 in a composite 22 during subsequent processing of the composite 22. Preferably, the composite 22 comprises multiple laminations 24 each consisting essentially of graphite fiber filaments 20 embedded in an epoxy matrix binder 26, and the subsequent processing consists essentially of compression molding such multiple laminations 24 into an aircraft engine fan blade 28.

The second preferred method of the invention includes sequential steps a) through e).

Step a) is portrayed in block 30 of FIG. 2 as "Dispose Optical Fiber In Composite Before Processing Composite". Step a) includes disposing at least a portion of an optical fiber 32 among the fiber filaments 20 in the composite 22 before the subsequent processing of the composite 22. Preferably, step a) also includes generally aligning at least a part of the portion of the optical fiber 32 with the fiber filaments 20 in the composite 22 before the subsequent processing of the composite 22.

Step b) is portrayed in block 34 of FIG. 2 as "Direct Light Into Optical Fiber During Processing". Step b) includes directing light (for example, light from a light emitting diode 36) from a first location 38 in the optical fiber 32 towards a second location 40 in the optical fiber 32 during the subsequent processing of the composite 22. A preferred light is spectral light having a predetermined frequency bandwidth. Preferably, the first location 38 is a first end of the optical fiber 32, the second location 40 is a second end of the optical fiber 32, and the first end and second end are disposed outside and spaced apart from the composite 22. More precisely, it is preferred that the first and second locations 38 and 40 also be centered on the longitudinal axis (i.e., the axis of elongation) of the optical fiber 32.

Step c) is portrayed in block 42 of FIG. 2 as "Reflect Light Back In Optical Fiber". Step c) includes reflecting the light from the second location 40 towards the first location 38 in the optical fiber 32. Preferably, such reflection is accomplished by providing one end (i.e., second location 40) of the optical fiber 32 with a fully reflective tip and by providing a glass capillary 44 to protect the fully reflective tip, as is known to those skilled in the art.

Step d) is portrayed in block 46 of FIG. 2 as "Measure Reflected Light Intensity In Optical Fiber During Processing". Step d) includes measuring the intensity of the light reflected from the second location 40 during the subsequent processing of the composite. Preferably, such measurement is accomplished by providing an optical coupler 47, a beam splitter 48, and light-intensity sensors 50 as is known to those skilled in the art and as is shown in FIG. 2. It is noted that, in this apparatus, light passes twice through the composite 22 before the light intensity is measured.

Step e) is portrayed in block 52 of FIG. 2 as "Ascertain If Measured Light Intensity Is Attenuated During Processing". Step d) includes ascertaining if the measured light intensity is attenuated at any time during the subsequent processing of the composite 22, such attenuation indicating misalignment at such time of the fiber filaments 20 during such subsequent processing of the composite 22. Preferably, such ascertaining is performed automatically by a suitably-programmed computer whose input is a series of paired times and measured light intensities, as can be appreciated by those skilled in the art. Applicants have found that ascertained attenuation of at least forty percent in step e) indicates misalignment of the fiber filaments 20 in the form of wrinkle formation during such subsequent processing of the composite 22.

In an exemplary method, which is also for minimizing such misalignment, the subsequent processing includes a process parameter which is controlled as a function of the attenuation ascertained in step e). Preferably, the subsequent processing includes compression molding (e.g., by mold 54 having two mold parts 56 and 58 which close towards each other at a controllable mold closure speed), and the process parameter includes mold closure speed. Here, the mold closure speed is reduced at the beginning of misalignment detection, and the mold closure speed is increased (up to some predetermined limit) as long as the beginning of misalignment was not being detected. It is noted that the two mold parts 56 and 58 never close enough to touch each other or to touch the optical fiber 32.

Applicants performed an experiment using the apparatus of FIG. 3 to carry out the method of FIG. 2. In the experiment, the optical fiber 32 had a 100 micron-diameter, 1.486 refractive-index core and a 1.457 refractive-index cladding at a wavelength of 0.85 microns, and the composite 22 had graphite fiber filaments 20 embedded in an epoxy matrix binder 26. The optical fiber 32 was placed in a channel cut in one of the laminations 24 of the composite 22. A heated end plate (omitted from FIG. 3 for clarity) was placed over each end of the mold 54 to prevent escape of the composite 22 during the compression molding. Each end plate had a longitudinally-outwardly-narrowing aperture which was filled with silicone rubber as a sealant and through which the optical fiber 32 passed out of the mold 54. During an approximately 150-minute mold closure processing step, the light intensity was attenuated by generally sixty percent during a less-than-one minute time interval during which the pressure (which was also being measured) in the composite 22 increased suddenly at the rate of nearly 1,000 psi/sec. Afterwards, the pressure quickly returned to normal. Post manufacturing inspection using x-ray CT confirmed that there was a series of wrinkles formed in the composite 22 in the vicinity of the optical fiber 32. This suggests that finely controlling the mold closure speed over a relatively small time window should avoid wrinkle formation in the composite 22, as can be appreciated by those skilled in the art.

Figure 4:
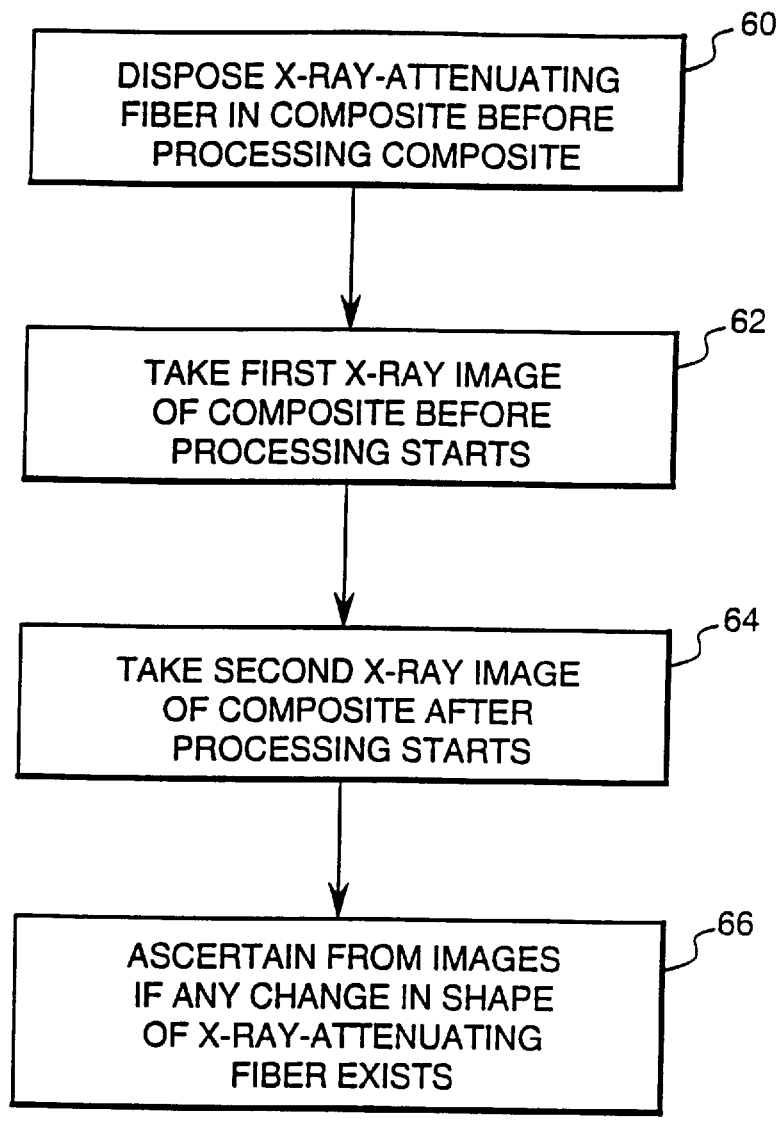
FIG. 4 is a flow chart of a third preferred method of the present invention for detecting fiber misalignment due to a composite processing step.

Referring once more to the drawings, FIG. 4 shows a flow chart of a third preferred method of the invention for detecting misalignment of initially-generally-aligned, x-ray-transparent fiber filaments in a composite due to subsequent processing of the composite. An example, without limitation, of x-ray-transparent fiber filaments in a composite is graphite fiber filaments which are embedded in an epoxy matrix binder.

The third preferred method of the invention includes sequential steps a) through d).

Step a) is portrayed in block 60 of FIG. 4 as "Dispose X-Ray-Attenuating Fiber In Composite Before Processing Composite". Step a) includes disposing at least a portion of an x-ray-attenuating fiber among the x-ray-transparent fiber filaments in the composite before the subsequent processing of the composite. An example, without limitation, of an x-ray-attenuating fiber is a fiber consisting essentially of (and preferably consisting of) gold. Preferably, step a) also includes generally aligning at least a part of the portion of the x-ray-attenuating fiber with the x-ray-transparent fiber filaments in the composite before the subsequent processing of the composite.

Step b) is portrayed in block 62 of FIG. 4 as "Take First X-Ray Image Of Composite Before Processing Starts". Step b) includes taking a first x-ray image of the composite showing the shape of the x-ray-attenuating fiber before the start of the subsequent processing of the composite.

Step c) is portrayed in block 64 of FIG. 4 as "Take Second X-Ray Image Of Composite After Processing Starts". Step c) includes taking a second x-ray image of the composite showing the shape of the x-ray-attenuating fiber after the start of the subsequent processing of the composite. Preferably, the second x-ray image is taken after the end of the subsequent processing of the composite.

Step d) is portrayed in block 66 of FIG. 4 as "Ascertain From Images If Any Change In Shape Of X-Ray-Attenuating Fiber Exists". Step c) includes ascertaining from the first and second x-ray images if any change in shape of the x-ray-attenuating fiber exists, such change in shape indicating misalignment of the x-ray-transparent fiber filaments in the composite due to the subsequent processing of the composite.

The foregoing description of several preferred methods of the invention has been presented for purposes of illustration. It is not intended to be exhaustive or to limit the invention to the precise methods disclosed, and obviously many modifications and variations are possible in light of the above teaching. It is intended that the scope of the invention be defined by the claims appended hereto.

We claim:

1. A method for detecting misalignment of initially-generally-aligned fiber filaments in a composite during subsequent processing of said composite, said method comprising the sequential steps of:

a) disposing at least a portion of an optical fiber among said fiber filaments in said composite before said subsequent processing of said composite;

b) directing light from a first location in said optical fiber towards a second location in said optical fiber during said subsequent processing of said composite;

c) measuring the intensity of said light from said second location during said subsequent processing of said composite; and d) ascertaining if the measured light intensity is attenuated at any time during said subsequent processing of said composite, said attenuation indicating misalignment at said time of said fiber filaments during said subsequent processing of said composite.

2. The method of claim 1, wherein step a) also includes generally aligning at least a part of said portion of said optical fiber with said fiber filaments in said composite before said subsequent processing of said composite.

3. The method of claim 2, wherein said first location is a first end of said optical fiber and said second location is a second end of said optical fiber.

4. The method of claim 3, wherein said first end and said second end are disposed outside and spaced apart from said composite.

5. The method of claim 4, wherein said light is spectral light having a predetermined frequency bandwidth.

6. The method of claim 5, wherein ascertained attenuation of at least forty percent in step d) indicates misalignment of said fiber filaments in the form of wrinkle formation during said subsequent processing of said composite.

7. The method of claim 6, wherein said composite comprises multiple laminations each consisting essentially of graphite fiber filaments embedded in an epoxy matrix binder, and wherein said subsequent processing consists essentially of compression molding said multiple laminations into an aircraft engine fan blade.

8. The method of claim 1 also for minimizing said misalignment, wherein said subsequent processing includes a process parameter which is controlled as a function of said attenuation ascertained in step d).

9. The method of claim 8, wherein said subsequent processing includes compression molding and said process parameter includes mold closure speed.

10. A method for detecting misalignment of initially-generally-aligned fiber filaments in a composite during subsequent processing of said composite, said method comprising the sequential steps of:

a) disposing at least a portion of an optical fiber among said fiber filaments in said composite before said subsequent processing of said composite;

b) directing light from a first location in said optical fiber towards a second location in said optical fiber during said subsequent processing of said composite;

c) reflecting said light from said second location towards said first location in said optical fiber;

d) measuring the intensity of said light reflected from said second location during said subsequent processing of said composite; and e) ascertaining if the measured light intensity is attenuated at any time during said subsequent processing of said composite, said attenuation indicating misalignment at said time of said fiber filaments during said subsequent processing of said composite.

11. The method of claim 10, wherein step a) also includes generally aligning at least a part of said portion of said optical fiber with said fiber filaments in said composite before said subsequent processing of said composite.

12. The method of claim 11, wherein said first location is a first end of said optical fiber and said second location is a second end of said optical fiber.

13. The method of claim 12, wherein said first end and said second end are disposed outside and spaced apart from said composite.

14. The method of claim 13, wherein said light is spectral light having a predetermined frequency bandwidth.

15. The method of claim 14, wherein ascertained attenuation of at least forty percent in step e) indicates misalignment of said fiber filaments in the form of wrinkle formation during said subsequent processing of said composite.

16. The method of claim 15, wherein said composite comprises multiple laminations each consisting essentially of graphite fiber filaments embedded in an epoxy matrix binder, and wherein said subsequent processing consists essentially of compression molding said multiple laminations into an aircraft engine fan blade.

17. The method of claim 10 also for minimizing said misalignment, wherein said subsequent processing includes a process parameter which is controlled as a function of said attenuation ascertained in step e).

18. The method of claim 17, wherein said subsequent processing includes compression molding and said process parameter includes mold closure speed.

* * * * *